United States Patent [19]
Hatfield et al.

[11] Patent Number: 5,865,750
[45] Date of Patent: Feb. 2, 1999

[54] METHOD AND APPARATUS FOR ENHANCING SEGMENTATION IN THREE-DIMENSIONAL ULTRASOUND IMAGING

[75] Inventors: William Thomas Hatfield, Schenectady, N.Y.; Todd Michael Tillman, West Milwaukee, Wis.; Michael John Harsh, Waukesha, Wis.; David John Muzilla, Mukwonago, Wis.; Anne Lindsay Hall, New Berlin, Wis.; Mir Said Seyed-Bolorforosh, Brookfield, Wis.; Michael J. Washburn, New Berlin, Wis.; David D. Becker, Milwaukee, Wis.

[73] Assignee: General Electric Company, Milwaukee, Wis.

[21] Appl. No.: 852,699
[22] Filed: May 7, 1997
[51] Int. Cl.$^6$ ........................................... A61B 8/00
[52] U.S. Cl. ........................................... 600/443; 128/916
[58] Field of Search .................... 600/443, 442; 128/916

[56] References Cited

U.S. PATENT DOCUMENTS

| | | | |
|---|---|---|---|
| 5,226,113 | 7/1993 | Cline et al. | 395/124 |
| 5,322,067 | 6/1994 | Prater et al. | 128/916 |
| 5,329,929 | 7/1994 | Sato et al. | 128/916 |
| 5,365,929 | 11/1994 | Peterson | 128/661.1 |
| 5,409,007 | 4/1995 | Saunders et al. | 128/916 |
| 5,474,073 | 12/1995 | Schwartz et al. | 128/661.1 |
| 5,485,842 | 1/1996 | Quistgaard | 128/660.07 |
| 5,582,173 | 12/1996 | Li | 128/660.07 |
| 5,588,435 | 12/1996 | Weng et al. | 600/443 |
| 5,655,535 | 8/1997 | Friemel et al. | 128/660.07 |

FOREIGN PATENT DOCUMENTS

WO 97/00482  1/1997  WIPO.

*Primary Examiner*—Marvin M. Lateef
*Assistant Examiner*—Moulin Patel
*Attorney, Agent, or Firm*—Dennis M. Flaherty; John H. Pilarski

[57] ABSTRACT

A method and an apparatus for three-dimensional imaging of ultrasound data by constructing projections of data from a volume of interest. An ultrasound scanner collects B-mode or color flow images in a cine memory, i.e., for a multiplicity of slices. A multi-row transducer array having a uniform elevation beamwidth is used to provide reduced slice thickness. The data from a respective region of interest for each of a multiplicity of stored slices is sent to a master controller, such data forming a volume of interest. The master controller performs an algorithm that projects the data in the volume of interest onto a plurality of rotated image planes using a ray-casting technique. The data for each projection is stored in a separate frame in the cine memory. These reconstructed frames are then displayed selectively by the system operator. Segmentation of three-dimensional projection images is enhanced by decreasing the thickness and increasing the resolution (i.e., decreasing the point spread function) of the two-dimensional slices from which the projections are derived. The slice thickness is decreased by increasing the elevational focus of the beam. The two-dimensional resolution is increased by opening the aperture, i.e., decreasing the f-number, and by increasing the bandwidth.

18 Claims, 5 Drawing Sheets

METHOD AND APPARATUS FOR ENHANCING SEGMENTATION IN THREE-DIMENSIONAL ULTRASOUND IMAGING

FIELD OF THE INVENTION

This invention generally relates to ultrasound imaging of the human anatomy for the purpose of medical diagnosis. In particular, the invention relates to apparatus for three-dimensional imaging of the human body and blood flowing therein by detection of reflected ultrasonic echoes reflected from the tissue or blood.

BACKGROUND OF THE INVENTION

The most common modes of diagnostic ultrasound imaging include B- and M-modes (used to image internal, physical structure), Doppler, and color flow (the latter two primarily used to image flow characteristics, such as in blood vessels). In conventional B-mode imaging, ultrasound scanners create images in which the brightness of a pixel is based on the intensity of the echo return. The color flow mode is typically used to detect the velocity of fluid flow toward/away from the transducer, and it essentially utilizes the same technique as is used in the Doppler mode. Whereas the Doppler mode displays velocity versus time for a single selected sample volume, color flow mode displays hundreds of adjacent sample volumes simultaneously, all superimposed on a B-mode image and color-coded to represent each sample volume's velocity.

Measurement of blood flow in the heart and vessels using the Doppler effect is well known. Whereas the amplitude of the reflected waves is employed to produce black and white images of the tissues, the frequency shift of backscattered waves may be used to measure the velocity of the backscatterers from tissue or blood. The backscattered frequency increases when blood flows toward the transducer and decreases when blood flows away from the transducer. Color flow images are produced by superimposing a color image of the velocity of moving material, such as blood, over the black and white anatomical image. The measured velocity of flow at each pixel determines its color.

The present invention is incorporated in an ultrasound imaging system consisting of four main subsystems: a beamformer 2 (see FIG. 1), a processor subsystem 4, a scan converter/display controller 6 and a master controller 8. System control is centered in master controller 8, which accepts operator inputs through an operator interface (not shown) and in turn controls the various subsystems. The master controller also generates the system timing and control signals which are distributed via a system control bus 10 and a scan control bus (not shown).

Figure 2:
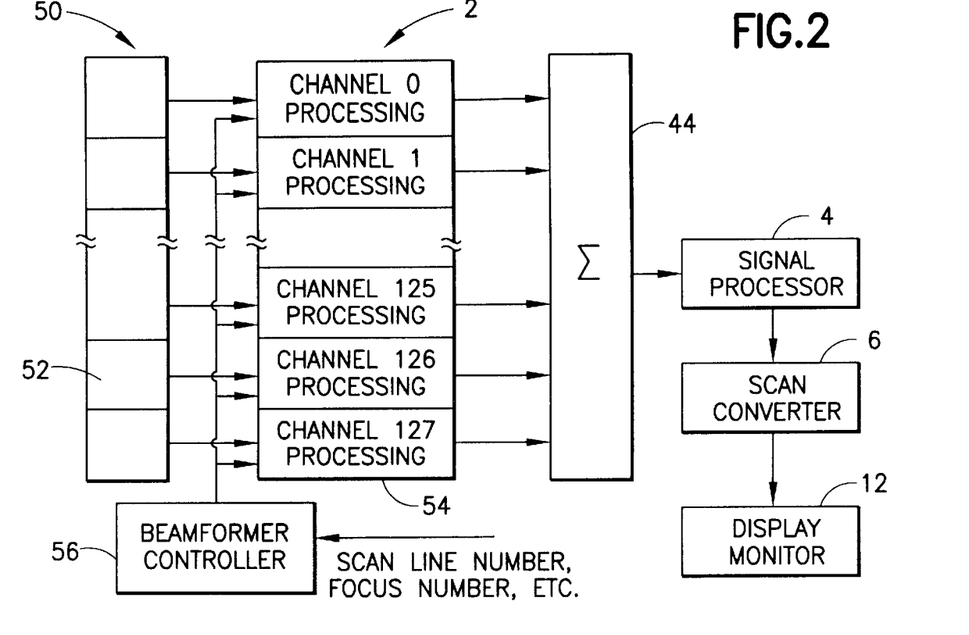
FIG. 2 is a block diagram of a typical 128-channel beamformer in a conventional ultrasound imaging system.

The main data path begins with the digitized RF inputs to the beamformer from the transducer. Referring to FIG. 2, a conventional ultrasound imaging system includes a transducer array 50 comprised of a plurality of separately driven transducer elements 52, each of which produces a burst of ultrasonic energy when energized by a pulsed waveform produced by a transmitter (not shown). The ultrasonic energy reflected back to transducer array 50 from the object under study is converted to an electrical signal by each receiving transducer element 52 and applied separately to the beamformer 2.

The echo signals produced by each burst of ultrasonic energy reflect from objects located at successive ranges along the ultrasonic beam. The echo signals are sensed separately by each transducer element 52 and the magnitude of the echo signal at a particular point in time represents the amount of reflection occurring at a specific range. Due to the differences in the propagation paths between an ultrasound-scattering sample volume and each transducer element 52, however, these echo signals will not be detected simultaneously and their amplitudes will not be equal. Beamformer 2 amplifies the separate echo signals, imparts the proper time delay to each, and sums them to provide a single echo signal which accurately indicates the total ultrasonic energy reflected from the sample volume. Each beamformer channel 54 receives the analog echo signal from a respective transducer element 52.

To simultaneously sum the electrical signals produced by the echoes impinging on each transducer element 52, time delays are introduced into each separate beamformer channel 54 by a beamformer controller 56. The beam time delays for reception are the same delays as the transmission delays. However, the time delay of each beamformer channel is continuously changing during reception of the echo to provide dynamic focusing of the received beam at the range from which the echo signal emanates. The beamformer channels also have circuitry (not shown) for apodizing and filtering the received pulses.

The signals entering the summer 44 are delayed so that they are summed with delayed signals from each of the other beamformer channels 54. The summed signals indicate the magnitude and phase of the echo signal reflected from a sample volume located along the steered beam. A signal processor or detector 4 converts the received signal to display data.

Figure 1:
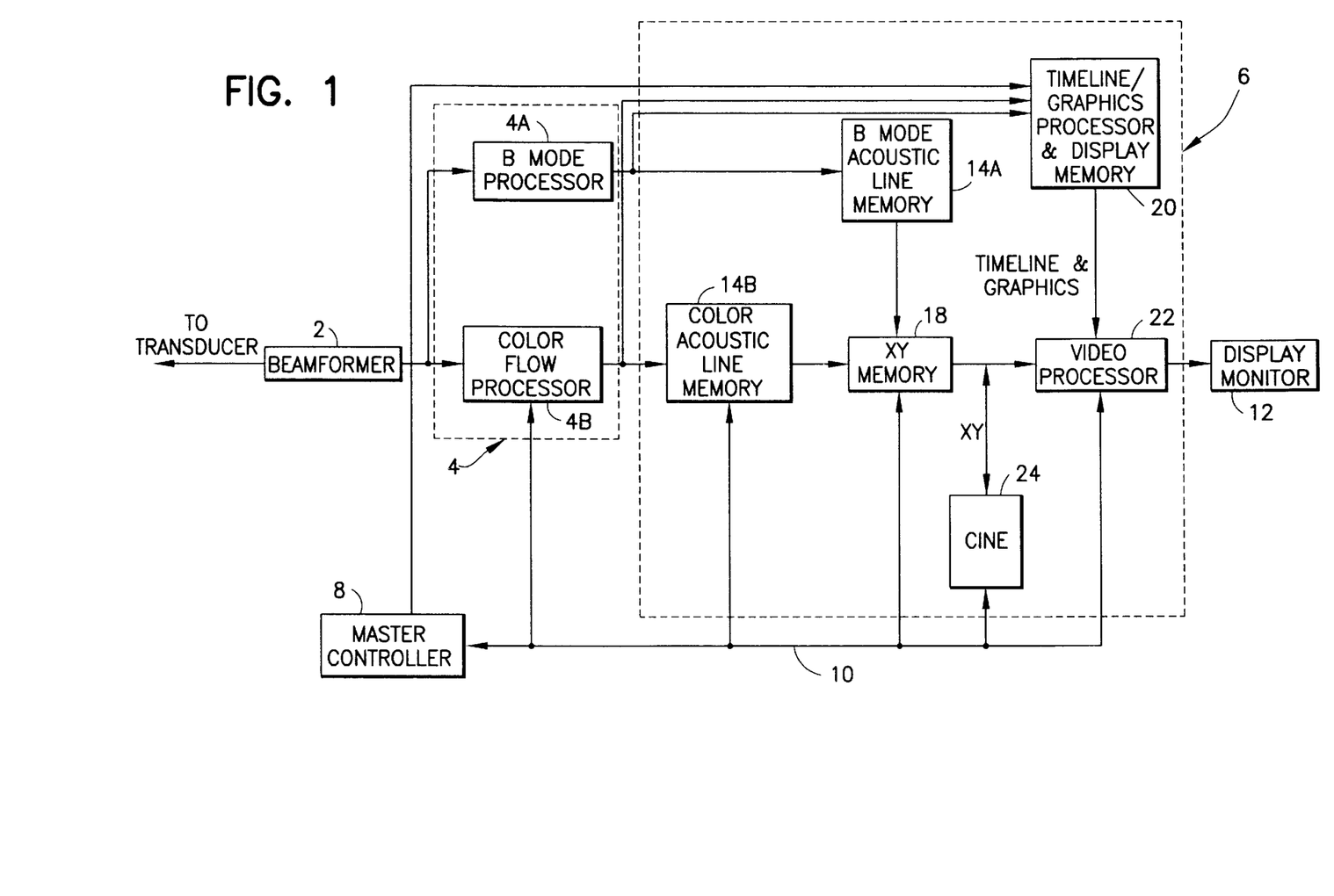
FIG. 1 is a block diagram showing the major functional subsystems within a real-time ultrasound imaging system.

The beamformer outputs two summed digital baseband receive beams. The baseband data is input to B-mode processor 4A and color flow processor 4B, where it is processed according to the acquisition mode and output as processed acoustic vector (beam) data to the scan converter/display processor 6. The scan converter/display processor 6 accepts the processed acoustic data and outputs the video display signals for the image in a raster scan format to a color monitor 22.

The B-mode processor 4A converts the baseband data from the beamformer into a log-compressed version of the signal envelope. The B function images the time-varying amplitude of the envelope of the signal as a grey scale using an 8-bit output for each pixel. The envelope of a baseband signal is the magnitude of the vector which the baseband data represent.

The frequency of sound waves reflecting from the inside of blood vessels, heart cavities, etc. is shifted in proportion to the velocity of the blood cells: positively shifted for cells moving towards the transducer and negatively for those moving away. The color flow (CF) processor 4B is used to provide a real-time two-dimensional image of blood velocity in the imaging plane. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. More specifically, the color flow processor produces velocity (8 bits), variance (turbulence) (4 bits) and power (8 bits) signals. The operator selects whether the velocity and variance or power are output to the scan converter 6. Ultimately, the output signal is input to a chrominance control lookup table which resides in the video processor 22.

The acoustic line memories 14A and 14B of the scan converter/display controller 6 respectively accept processed digital data from processors 4A and 4B and perform the coordinate transformation of the color flow and B-mode data from polar coordinate (R-θ) sector format or Cartesian coordinate linear array to appropriately scaled Cartesian coordinate display pixel data stored in X-Y display memory 18. In B mode, the intensity data is stored in X-Y display memory 18, each address storing three 8-bit intensity pixels. In color flow mode, the data is stored in memory as follows: intensity data (8 bits), velocity or power data (8 bits) and turbulence data (4 bits).

The scan converter 6 converts the acoustic image data from polar coordinate (R-θ) sector format or Cartesian coordinate linear array to appropriately scaled Cartesian coordinate display pixel data at the video rate. This scan-converted acoustic data is then output for display on display monitor 12. In the B mode, the monitor images the time-varying amplitude of the envelope of the signal as a grey scale, i.e., the brightness of a pixel is based on the intensity of the echo return. In the color flow mode, if movement is present, e.g., blood flowing in an artery, a Doppler shift in the return signal is produced proportional to the speed of movements. The display images the flow of blood, i.e., the Doppler shift using different colors, e.g., red for flow toward and blue for flow away from the transducer. In power Doppler imaging, the power contained in the returned Doppler signal is displayed.

Successive frames of color flow or B-mode data are stored in cine memory on a first-in, first out basis. Storage can be continuous or as a result of an external trigger event. The cine memory is like a circular image buffer that runs in the background, capturing image data that is displayed in real time to the user. When the user freezes the system, the user has the capability to view image data previously captured in cine memory. The graphics data for producing graphics overlays on the displayed image is generated and stored in the timeline/graphics processor and display memory 20. The video processor 22 multiplexes between the graphics data, image data, and timeline data to generate the final video output in a raster scan format on video monitor 12. Additionally it provides for various greyscale and color maps as well as combining the greyscale and color images.

Conventional ultrasound scanners create two-dimensional images of a "slice" through an area of the anatomy. Two-dimensional ultrasound images are often hard to interpret due to the inability of the observer to visualize the representation of the anatomy being scanned. However, if the ultrasound probe is swept over an area of interest and two-dimensional images are accumulated to form a three-dimensional volume, the anatomy is easier to visualize. The data may be manipulated in a number of ways, including volume or surface rendering. In addition, the data may be resampled and displayed in planes other than the ones in which the data was originally collected. This allows the user to obtain views of the anatomy that may not be possible given the anatomy and the inability to properly position the probe.

The above techniques have been used to display ultrasound data with varying degrees of success. One problem is that lack of resolution (both spatial and contrast), coupled with speckle and noise in the two-dimensional images make it difficult to properly segment the projected image. The lack of resolution in two-dimensional images is due to a number of factors, including an inability to maintain uniform focus of the beam over a large range, a lack of bandwidth and dynamic range, and a high f-number of the system. Another problem has been the limited range of elevational focus of the beam produced by a single-row, fixed single-focus transducer array. The source data slices used in the reconstruction of a three-dimensional image vary in thickness due to the nonuniform elevation beamwidth. Therefore, the reconstructed images successively degrade as projections or resampled images approach an angle perpendicular to the plane of acquisition. Thus there is a need to lower the f-number and increase the bandwidth of the system, to improve both spatial and contrast resolution of the two-dimensional images, and a further need to control the elevational focus of the ultrasound beam over a greater range, to obtain a much thinner slice of more uniform thickness, enabling improved segmentation in three-dimensional imaging.

SUMMARY OF THE INVENTION

The present invention is a method and an apparatus for three-dimensional imaging by projecting ultrasound data acquired by scanning a volume of interest. The object volume is scanned using a multiplicity of slices having a substantially uniform thickness. The ultrasound scanner collects B-mode or color flow mode images in a cine memory on a continuous basis or in response to an external trigger event, i.e., for a multiplicity of slices. The sample volume data from a respective region of interest for each slice is sent to a master controller, such data forming a volume of interest. The master controller performs an algorithm that projects the sample volume data in the volume of interest on a plurality of rotated image planes using a ray-casting technique. The sample volume data for each projection is stored, optionally with the portion of the last background frame lying outside the region of interest, in a separate frame in the cine memory. These reconstructed frames are then displayed selectively by the system operator.

In accordance with the present invention, segmentation of three-dimensional projection images is enhanced by decreasing the thickness and increasing the resolution (i.e., decreasing the point spread function) of the two-dimensional slices from which the projections are derived. The slice thickness is decreased by increasing the elevational focus of the beam. The two-dimensional resolution is increased by opening the aperture, i.e., decreasing the f-number, and by increasing the bandwidth. The result is an exceedingly small voxel size.

The method of the invention employs a number of techniques, including the use of multiple transmit focal zones and transmit and receive apertures having low f-numbers, i.e., 0.5 to 2.0 for B mode and 1.0 to 3.0 for color flow mode. Using multiple focal zones with low f-numbers allows for tight focusing over a larger depth-of-field. Furthermore, unique waveforms and unique gain curves can be used for different focal zones. In particular, the waveform center frequency can be decreased with increasing depth to provide less attenuation and more penetration, while the waveform burst length can be increased with increasing depth to improve sensitivity at greater depths.

In B-mode imaging, multiple focal zones are fired for each acoustic frame and the out-of-focus data is discarded during beamforming. In color flow mode imaging, each focal zone is fired on a separate acoustic frame and an adaptive frame averaging algorithm is used to blend together the in-focus data from each of these acoustic frames.

A uniform elevation beamwidth is achieved through use of a multi-row transducer array having a central row of transducer elements arranged between first and second outer rows of paired transducer elements. Preferably, the central row is made up of elements having an area smaller than the combined area of the paired elements of the outer rows. This geometry provides excellent elevation performance (thinner and more uniform image slice, greater contrast resolution), especially in the very near field. Preferably, the array has five rows and a multi-focal lens, the combined area of each pair of elements in the outermost rows being greater than the area of each element of the central row and greater than the combined area of each pair of elements in the intermediate rows.

In accordance with the preferred embodiment of the invention, the elevational focus, the waveform center frequency and the waveform burst length are each changed as a function of depth. One can therefore program a number of focal zones and achieve a better point spread function over the entire image. In addition, by adjusting the beamforming parameters, it is possible to increase the number of active elements and thereby open the aperture of the probe, i.e., lower the f-number. This has the effect of lowering the sidelobes, producing a better peak-to-noise floor ratio, which improves contrast resolution. A wider dynamic range can be achieved by increasing the bit width of the data in the ultrasound system and lowering the overall noise floor of the system.

The ultrasound imaging system in accordance with one preferred embodiment of the invention comprises a digital beamformer which allows the beamforming parameters of the system to change the focus of the beam in both azimuth and elevation with depth. A second preferred embodiment comprises a digital beamformer which allows the beamforming parameters of the system to change the azimuthal focus of the beam and a fixed-focus lens to change the elevation focus with depth. Thus, a narrower and more uniform beamwidth can be maintained over a much larger range. Additionally, the digital beamformer allows the aperture of the probe to be controlled to produce a wider aperture and therefore a lower f-number.

DETAILED DESCRIPTION OF THE PREFERRED EMBODIMENTS

Figure 3:
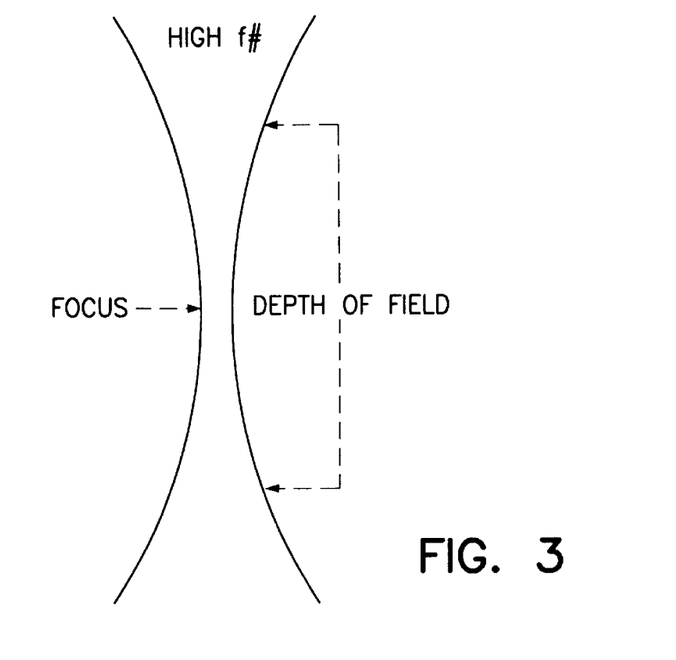
FIG. 3 is a schematic depicting the acoustic beam profile which results when the ultrasound transducer array has an aperture with a relatively high f-number.
Figure 4:
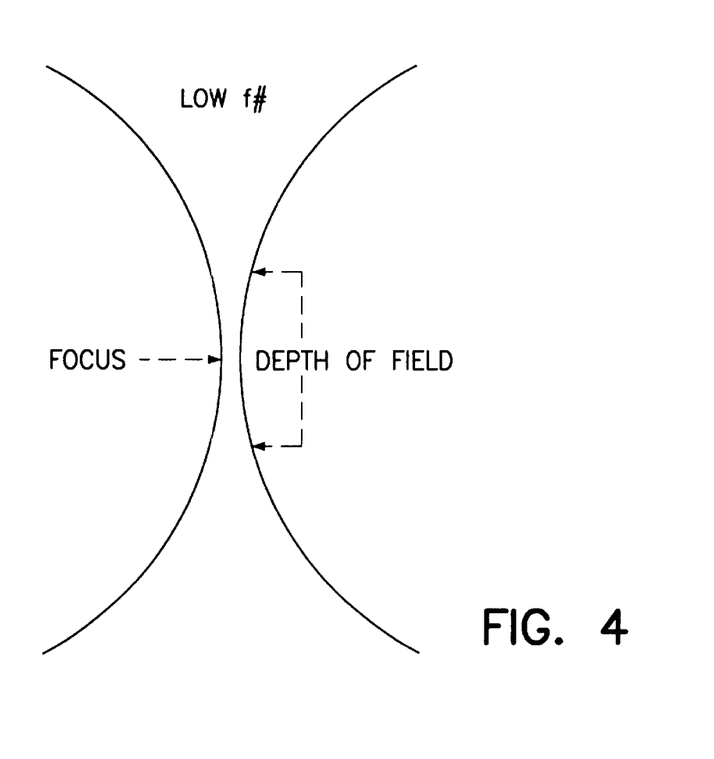
FIG. 4 is a schematic depicting the acoustic beam profile which results when the ultrasound transducer array has an aperture with a relatively low f-number.

In accordance with one aspect of the present invention, low transmit and receive f-numbers (i.e., wide apertures) are used to enhance spatial resolution. The effect on the acoustic beam profile of using low f-number apertures is depicted in FIGS. 3 and 4. FIG. 3 shows the result of using a higher f-number (smaller aperture). Lateral focusing is not very sharp at the focal point even though the depth-of-field is fairly large in the range dimension. The beam shown in FIG. 4 is the result of using a lower f-number (greater aperture). Lateral focusing is tighter at the focal point and the depth-of-field is narrower. In accordance with the preferred embodiments of the invention, the range of f-numbers is 0.5 to 2.0 for B mode and 1.0 to 3.0 for color flow mode.

Figure 5:
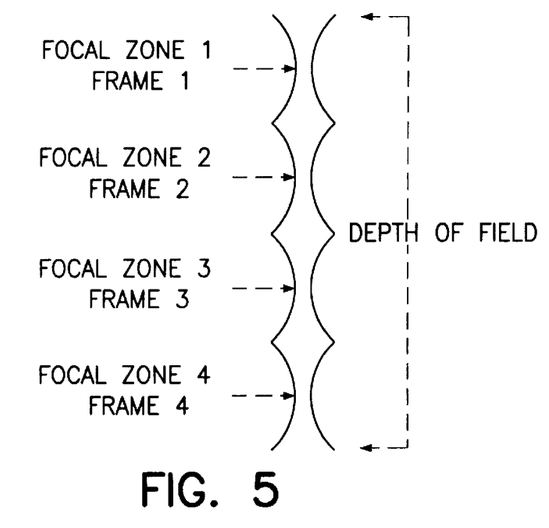
FIG. 5 is a schematic depicting the acoustic beam profile which results when multiple transmit focal zones are used in accordance with the present invention.

In accordance with a further feature of the present invention, multiple transmit focal zones are used. Using multiple focal zones with low f-numbers solves the depth-of-field problem, allowing for tight focusing over a larger depth-of-field as shown in FIG. 5. In accordance with the system of the present invention, 1 to 8 focal zones can be used along each scan line. The firing of multiple focal zones, in accordance with the invention, presents a challenge for the already frame-rate-limited color imaging mode, since complete packets need to be fired for each focal zone. This challenge is overcome by firing each focal zone on a separate acoustic frame. Thus, the focal zone position is changing from frame to frame.

In addition, unique waveforms can be used for each focal zone. In the near-field, the transmit waveforms have relatively short burst lengths. For example, in B mode imaging in accordance with a preferred embodiment of the invention, the transmit waveforms in the near field preferably comprise only one pulse, which is repeated at the pulse repetition frequency. The use of shorter-burstlength waveforms results in better axial resolution while trading off sensitivity (less energy in the waveform), which can be compensated for by using a larger aperture in the near-field. Longer-burstlength waveforms are often needed in the far field to achieve the required penetration. In accordance with a further aspect of the invention, the transmit waveforms can vary from focal zone to focal zone. Using a lower-frequency waveform results in more penetration at depth and using a higher-frequency waveform results in better near-field resolution.

For B mode imaging of the abdomen, the system in accordance with the invention transmits in a range of 2.5–5 MHz using an aperture having an f-number of 1.0. For B mode imaging of smaller body parts, the system in accordance with the invention transmits in a range of 8.75–12 MHz using an aperture having an f-number of 1.5. The preferred number of focal zones is 2 to 8.

In the color flow mode, the preferred range for the demodulation frequency is 1.25 to 8 MHz, depending on the probe, and the preferred number of transmit cycles (i.e., the burst length) for each focal zone is 2 to 8 cycles, depending on the transmit focal depth, center frequency and desired axial resolution. For example, in accordance with one high-resolution beam-forming setup for the color flow mode, the demodulation frequency is 5 MHz for all focal zones; the number of transmit cycles is 3 for the first 10 focal zone positions (e.g., covering from 0.4 to 3.1 cm); and the number of transmit cycles is 4 for the 11th and 12th focal zone positions (e.g., at 3.4 and 3.7 cm, respectively).

In accordance with yet another aspect of the invention, unique gain curves are used for each focal zone. The term "gain curve" as used herein refers to the manner in which the receiver gain of the system changes with depth. At deeper depths more gain is needed than at shallower depths because attenuation of the acoustic signal is greater at deeper depths. To create a relatively uniform image over depth (uniform in gain), more gain typically needs to be applied at deeper depths. However, in accordance with the invention, most of the energy of the transmitted signal appears at or near the transmit focal zone. Gain matching is done using a unique gain curve for each focal zone. The gain curves are a set of numbers in a file for each focal zone, which numbers represent the gain applied to the signal in that stage of the processing. These gain curves are applied on the equalization board, which is part of the beamformer.

In the color flow mode, the gain is adjusted so the signal is somewhat higher at the focal zone and less away from the focal zone. In this way, the color flow frame averaging algorithm captures the higher in-focus signal and minimizes out-of-focus contributions from the "away" focal zones.

When scanning in the color flow mode, a two-dimensional image is created by firing one vertical vector after another from left to right to build up a single two-dimensional set of pixel data which will form the image. This set of vertical data vectors is known as an acoustic frame of color flow data. When scanning in the color flow mode, as each acoustic frame of color flow data is acquired, it is processed further while the next acoustic frame of data is being acquired. In accordance with the concept of the present invention, each acoustic frame has one transmit focal zone position for its vectors which can be different from the focal zone position of the previous and subsequent acoustic frames. An adaptive frame averaging algorithm is used to blend together the in-focus data from each of these acoustic frames in preparation for display. In accordance with the preferred embodiment, the focal zones are combined using a non-linear, data-dependent frame-averaging algorithm. The advantage of this method is that there is no further reduction of real frame rate, since no additional firings are needed over the traditional single-focus color mode. Any given flow signal level in the image would be stronger in amplitude when the focal zone nearest to that flow was transmitted. That same flow would appear weaker in amplitude when the other "away" focal zones fired. The frame averaging algorithm takes advantage of this fact by persisting the stronger, in-focus flow amplitude more than the weaker out-of-focus flow amplitude, creating a resultant displayed image which gives both higher spatial resolution and greater sensitivity. This works well in the velocity mode also since weaker out-of-focus flow, away from the transmit focal zone, tends to drop below the velocity mode amplitude threshold and is not displayed. The strong in-focus flow at and near the transmit focus tends to be above this threshold and therefore the velocity signal gets displayed.

Figure 6:
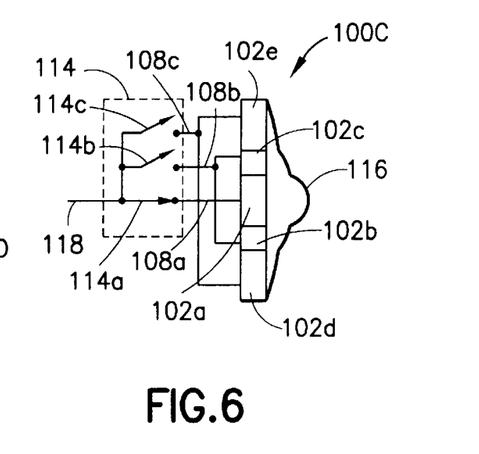
FIG. 6 is an elevation cross-sectional view of a multi-row transducer array which can be employed in the three-dimensional ultrasound imaging system of the present invention to achieve changing elevational focus with increasing depth.

In accordance with the preferred embodiment of the invention, optimum elevation performance (minimum image slice thickness and maximum contrast resolution) is achieved with multi-row transducer arrays having a shorter (i.e., lesser height) central row and taller (i.e., greater height) outermost rows. The outermost rows are also taller in the elevation direction than any intermediate rows.

As one example of the application of the above array design principles, FIG. 6 shows a 5-row 1.25D array with a small central row 102a and large outermost rows 102d and 102e, which can be employed in the system of the present invention. The row edges are at distances (¼, ½, 1)$Y_{max}$ from the array centerline. Thus, the paired elements of intermediate rows 102b and 102c have an area equal to the area of each element of central row 102a; and the paired elements of outermost rows 102d and 102e have an area equal to twice the area of each element of central row 102a. The ultrasound pulses are transmitted through a multi-focus lens 116 having lens foci of 35, 65 and 90 mm. The central section of lens 116, having a 35 mm focal length, focuses the ultrasound beams transmitted by central row 102a; the adjacent lens sections (65 mm focal length) focus the beams respectively transmitted by rows 102b and 102c; and the outermost lens sections (90 mm focal length) focus the beams respectively transmitted by outermost rows 102d and 102e. The multi-focus lens improves the uniformity of the elevation beam profile by focusing the central row in the near field, where only the central row is active, and the outer rows in the far field, which is the only region where they are active.

In the 1.25D array shown in FIG. 3, a multiplicity of multiplexers 114 are respectively connected to a corresponding multiplicity of signal leads 118 (only one multiplexer and one signal lead are seen in FIG. 3). Each signal lead 118 is connected to a respective beamformer channel (not shown in FIG. 3). Each multiplexer 114 has three internal switches which multiplex signal leads 108a–108c to connect with signal lead 118. Each column of transducer elements is connected to a respective set of such signal leads: the central row element 102a being connected to signal lead 108a; the paired elements 102b, 102c of the intermediate rows being connected in to signal lead 108b; and the paired elements 102d, 102e of the outermost rows being connected in to signal lead 108c. In practice, the pairing of elements (i.e., connection of 102b to 102c and of 102d to 102e) are connected together within the probe head, whereas the multiplexers may be located within the probe head, at the console end of the probe cable or within the system console itself.

Because changing the state of the multiplexer switches generates noise, use of this probe typically requires three transmit-receive cycles per beam. With the multiplexer switches 114a for the center row of elements 102a closed and switches 114b and 114c open, the transmit delays are set to provide azimuthal focusing in the near field, and the near portion of the beam data is acquired. Next, switches 114a and 114b are closed, the transmit and receive delays are reconfigured, and the mid-field data is acquired using rows 102a, 102b and 102c. Finally, all the multiplexer switches are closed, the transmit and receive delays are reconfigured, and the far-field data is acquired using rows 102a–102e. Data from the three zones are spliced together in the imaging system, with care being taken to compensate for the change in sensitivity at the transition. Thus, in accordance with the present invention, the beam focus in both the elevation and azimuth directions is changed as a function of depth.

As the imaging depth increases from the near toward the far field, more of the rows of transducer elements become involved. To obtain uniform elevation performance over a maximum range, one would prefer to have the effective focal distance of the array increase as the active aperture increases. With the array shown in FIG. 6, all of the elevation focusing is provided by the acoustic lens. To increase the focus position as the aperture increases, a multi-focus lens is used.

In accordance with a variant of the preferred embodiment shown in FIG. 6, each transducer element in the central row 102a has a predetermined area, each pair of transducer elements in outer rows 102d and 102e have a first combined area greater than the predetermined area, and each pair of transducer elements in intermediate rows 102b and 102c have a second combined area greater than the predetermined area, but less than the first combined area.

Elevational beam control for the array shown in FIG. 6 is accomplished only with a lens and a multiplexer. All elements within each elevational column of the array are connected to the same beamforming channel and share the same electronic time delay and shading. However, 1.5D arrays could also be used in the present invention to achieve elevational focus. 1.5D arrays use dynamic focusing and shading to control the elevational beam. With elevational symmetry (no steering), this requires an independent beamforming channel for each set of paired elevational elements.

The above-described techniques are employed to obtain a stack of frames of pixel data acquired from an object volume. As the probe is swept over an area of the anatomy, either by free-hand scanning or using a system for moving the probe, a three-dimensional volume may be obtained. The position of each frame image with respect to the next may be determined in a number of ways. The probe may be scanned in some manner, such as by moving the probe linearly, by rocking the probe through an angle or by rotating the probe through an angle perpendicular to the probe face. If the probe is translated at a constant rate, over a known distance or through a known range of angles, the distance between each image can be easily determined. The distance the probe was translated may be determined in numerous ways, e.g., by simply measuring the distance with a suitable measurement device, using markers on or within the anatomy, or attaching position sensors to the probe. The probe may also be moved along an arbitrary path and the data from position sensors mounted on the probe may be used to determine the location of each image. These images may then be placed on a Cartesian volume. In addition, the probe may be fixed in a device which moves the probe along a known path.

Figure 7:
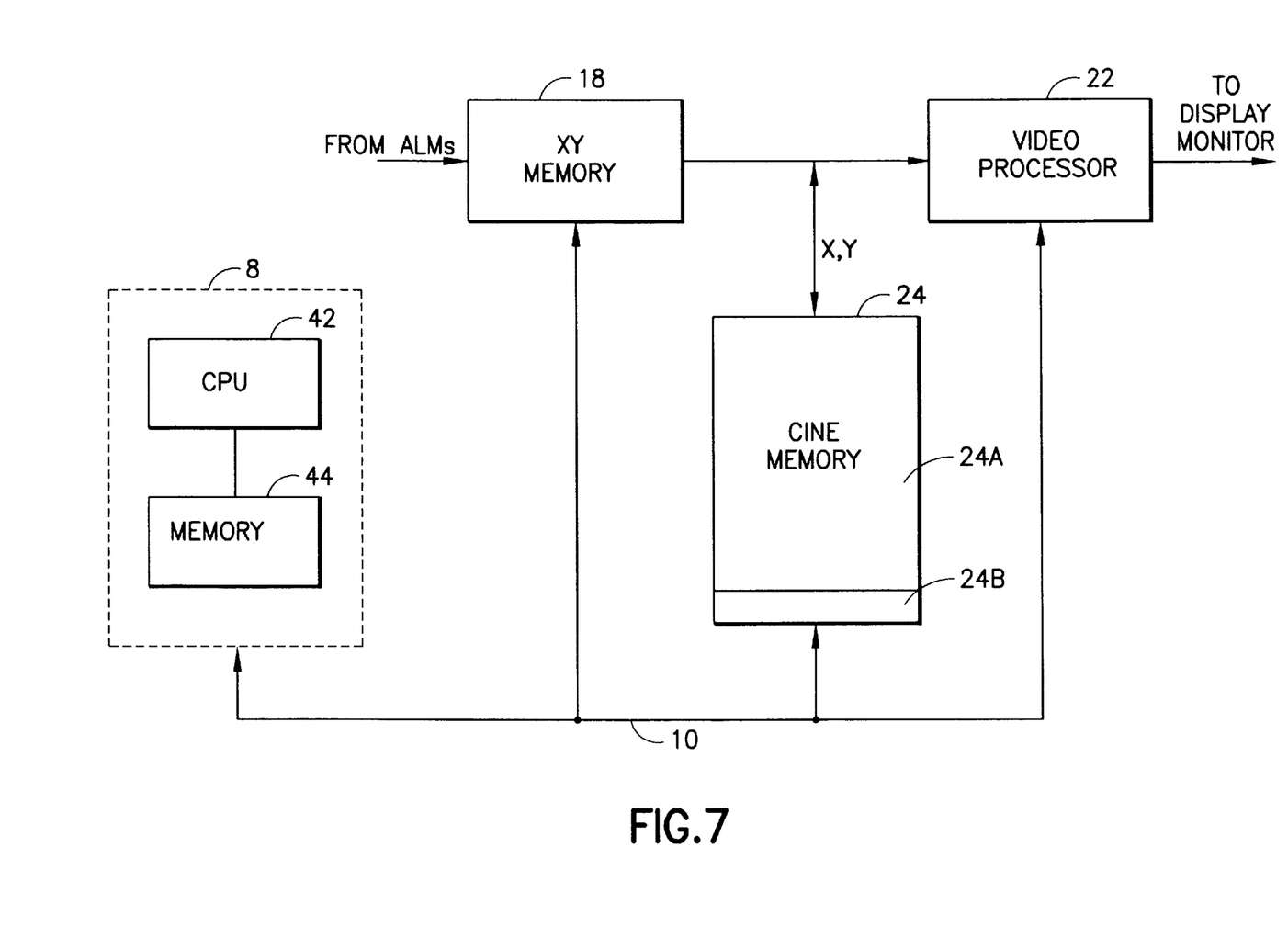
FIG. 7 is a block diagram showing the means for reconstructing frames comprising successive volumetric projections of pixel data in accordance with a preferred embodiment of the present invention.
Figure 8:
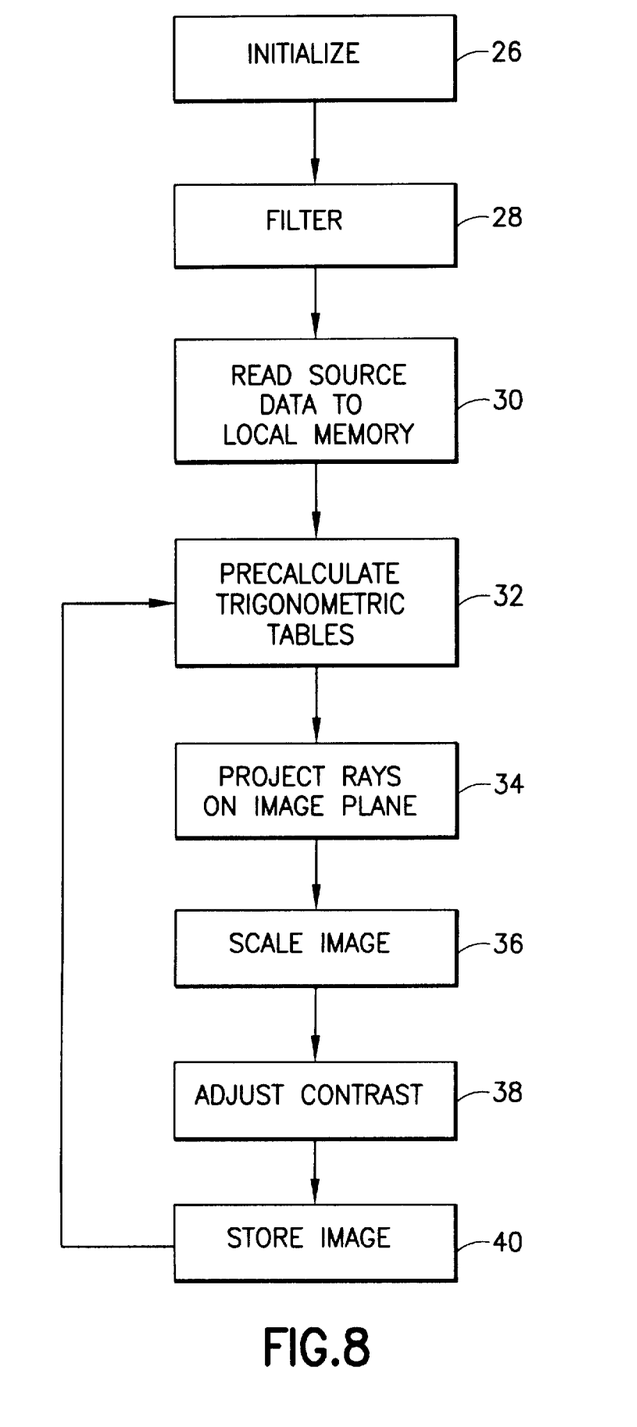
FIG. 8 is a flowchart showing the steps of an algorithm for reconstructing frames comprising successive volumetric projections of intensity and velocity or power pixel data in accordance with the preferred embodiment of the present invention.

Referring to FIGS. 7 and 8, the method for projecting sample volume data into three-dimensional images in accordance with the invention will be disclosed. As seen in FIG. 7, the master controller 8 comprises a central processing unit (CPU) 42 and a random access memory 44. The CPU 42 has read only memory incorporated therein for storing routines used in transforming the acquired volume of sample volume data into a multiplicity of projection images taken at different angles. The CPU 42 controls the XY memory 18 and the cine memory 24 via the system control bus 10. In particular, CPU 42 controls the flow of data from XY memory 18 to video processor 22 and to cine memory 24, and from cine memory 24 to video processor 22 and to CPU 42 itself. Each frame of pixel data, representing one of a multiplicity of scans or slices through the object being examined, is stored in the XY memory 18 and in the next cycle is transmitted to video processor 22 and to cine memory 24. A stack of frames, representing the scanned object volume, is stored in section 24A of cine memory 24. During initialization (see step 26 in FIG. 8), the CPU 42 retrieves from cine memory section 24A only the pixel data corresponding to an object volume of interest. This is accomplished by retrieving only the pixel data in a region of interest from each stored frame acquired from any scan intersecting the object volume of interest. In other words, the pixel data corresponding to the region of interest from each one of a stack of successive frames forms a source data volume of interest.

As seen in FIG. 8, the intensity data in the pixel data set corresponding to the object volume of interest is optionally filtered (step 28) prior to projection in order to smooth speckle noise and reduce artifacts. This prevents the loss of data due to speckle noise during projection. For example, blood vessels are less echogenic than the surrounding tissue. Therefore vessels can be imaged using minimum intensity projections. Alternatively, in the reverse video/minimum mode, the intensity data is inverted to make the vessels bright instead of dark. The vessels can then be imaged using maximum intensity projections. To prevent the selection of maximum intensities which are bright speckle as opposed to desired pixel data, a filter can be used to remove such bright speckle intensities prior to projection. The source data volume retrieved from the cine memory 24 may be filtered by CPU 42 using, e.g., a 3×3 convolution filter having a 111 141 111 kernel, i.e., the central pixel of intensity data in each 3×3 pixel array in each slice or frame is replaced by an intensity value proportional to the sum of four times the value of the central pixel plus the sum of the values of the eight pixels surrounding that pixel. The filtered source data volume is then stored in memory 44 (step 30). In a similar manner, a convolution filter can be used to remove black holes in an image prior to minimum intensity projection.

Next the CPU 42 performs a series of transformations using the ray casting algorithm disclosed in U.S. Pat. No. 5,226,113, the contents of which are specifically incorporated by reference herein. The successive transformations represent maximum, minimum or averaged intensity, velocity or power projections made at angular increments, e.g., at 10° intervals, within a range of angles, e.g., +90° to −90°. However, the angular increment need not be 10°; nor is the invention limited to any particular range of angles.

In accordance with the ray casting technique employed in the present invention, volumetrically rendered projection images of a sample are displayed from any arbitrary viewing angle by scanning an object volume using an ultrasound transducer array having substantially uniform elevation beamwidth. The sample volume is scanned in such a manner as to create a series of stacked, contiguous slices, each of which contains the same number of object volume elements (voxels). Each voxel has a rectangular profile in the sheet plane (say, the X-Y plane); while the complementary sides may be of equal length, so that this profile may be square, the sheet thickness is generally greater than the length of either side.

Each object voxel is analyzed and the data value (intensity, velocity or power) thereof is placed in a corresponding data voxel of a data volume. The data volume is a simple cubic lattice, even though the thickness of each object slice and each object voxel face size (the size of the voxel in the X-Y plane) will generally not be the same.

In accordance with a known technique employed by CPU 42, an image of the object volume is projected (step 34 in FIG. 8) by ray casting toward an image plane from a lattice point in each data voxel. For convenience, the lattice point may, for example, be the data voxel vertex closest to the data volume origin. While all rays impinge upon some portion of the image plane, only those rays falling within the image plane pixel under consideration are allowed to contribute to the data for that image plane pixel. For a maximum pixel projection, each projected value is compared with the currently stored value and the larger of the two values is placed in storage for that pixel 60a. For a minimum pixel projection, the smaller of the two values is stored. As each voxel in the selected data volume is sequentially entered and projected toward the image plane, a data volume voxel is eventually projected along its associated ray and does not impinge within the desired pixel, so that its data value (e.g., intensity) is not compared to the data value presently stored for that pixel. The maximum data value for that pixel is now established, for that projection of the data at the particular three-dimensional angle of view. All data values are reset to zero when a new projection is to be taken. Thus, each of the image plane pixels is reset at the start of an image projection procedure, and all of the data volume voxels (in the entire space or in the selected portion, as set by the portion of the object volume selected) are individually and sequentially scanned. The data value in each data voxel is projected through an associated ray to impinge upon the image plane in one pixel thereof, with the maximum value in each pixel being compared between the present value of the raycasted data volume voxel, to determine the larger thereof, which larger value is then stored as part of the maximum value image.

In accordance with another aspect of the foregoing technique, the data projection is scaled (step 36 in FIG. 8) and any anisotropy between the object volume and the image plane is removed by only a single set of calculations after back projection is complete. Because the object volume is a real volume while the data volume is an abstract concept, it is necessary to determine the amount of distortion of the data projection due to the presentation of the cubic data volume lattice at a different angle, in a first plane, than the angle at which an arbitrary viewing direction will be positioned with respect to both the object volume and data volume. The apparent dimensions of each voxel are going to change as the effective elevation angles change. If the aspect ratio (defined as the ratio of the actual slice thickness in the object volume to the actual pixel size in the same object volume) is not unity (i.e., is greater than unity), then the angles of elevation will be different, and the effective elevation angle in the data volume will be different than the actual elevation angle in the object volume. The data is then rotated in accordance with an object elevation angle. Thereafter, the projected data can be scaled to have the correct height (if rotation is about the horizontal axis) in the object volume, by multiplication of all projected data heights by an elevation scale factor. The elements of a 3×3 rotational matrix can be determined (as disclosed in U.S. Pat. No. 5,226,113), and these relationships are used to determine the data volume-to-image plane transformations. After the data is projected onto the image plane, the image is scaled to correct for the effect of the anisotropic object voxels. The factors in the rotational matrix can be precalculated (step 32 in FIG. 8) at the beginning of a projection and used for all rotation calculations.

In accordance with a further aspect of the invention, prior to display the scaled image plane data is mapped to achieve a desired brightness and contrast range (step 38 in FIG. 8).

The method shown in FIG. 8 can be applied to B-mode intensity data or to color flow velocity or power data for the data volume of interest retrieved from the cine memory. Each pixel in the projected image includes the transformed intensity data and the transformed velocity or power data derived by projection onto a given image plane. In addition, at the time when the cine memory was frozen by the operator, the CPU 42 optionally stores the last frame from the XY memory 18 at multiple successive addresses in section 24B of cine memory 24. The projected image data for the first projected view angle is written into the first address in cine memory section 24B, so that the projected image data in a region of interest is superimposed on the background frame. This process is repeated for each angular increment until all projected images are stored in cine memory section 24B, each projected image frame consisting of a region of interest containing transformed data and optionally a background perimeter surrounding the region of interest consisting of background frame data not overwritten by region-of-interest transformed data. The background image makes it clearer where each displayed projection is viewed from. The operator can then select any one of the projected images for display. In addition, the sequence of projected images can be replayed on the display monitor to depict the object volume as if it were rotating in front of the viewer.

The foregoing preferred embodiments have been disclosed for the purpose of illustration. Variations and modifications will be readily apparent to those skilled in the arts of ultrasound imaging or computer graphics. All such variations and modifications are intended to be encompassed by the claims set forth hereinafter.

We claim:

1. A system for three-dimensional imaging of ultrasound scattering matter in an object volume, comprising:

an ultrasound transducer array for transmitting ultrasound beams and detecting ultrasound echoes reflected from the object volume;

first means for changing the azimuthal focusing of said transducer array to achieve changes in focal depth;

second means for changing the elevational focusing of said transducer array as a function of said focal depth;

third means for changing a characteristic of the waveform used to drive said transducer array as a function of said focal depth;

means for coordinating said first, second and third changing means to acquire a source volume of pixel data derived from sample volumes in said object volume;

memory means for storing said source volume of pixel data;

means for retrieving a set of pixel data from said memory means corresponding to a volume of interest in the object volume;

means for projecting said pixel data set onto a first image plane, thereby forming a projected data set representing a first projected image;

a display monitor; and means for displaying said first projected image on said display monitor.

2. The system as defined in claim 1, wherein said pixel data comprises B-mode intensity data.

3. The system as defined in claim 1, wherein said pixel data comprises velocity data.

4. The method as defined in claim 1, wherein said pixel data comprises power Doppler data.

5. The system as defined in claim 1, wherein said third changing means increases the burst length of the transmit waveform with an increase in focal depth.

6. The system as defined in claim 1, wherein said third changing means decreases the frequency of the transmit waveform with an increase in focal depth.

7. The system as defined in claim 1, wherein said transducer array is operated with a lateral aperture having an f-number less than 1.5.

8. The system as defined in claim 1, wherein said second changing means controls said transducer array to have an elevation aperture which is increased with an increase in focal depth.

9. The system as defined in claim 1, further comprising:

means for projecting said pixel data set onto a second image plane which is rotated relative to said first image plane, thereby forming a projected data set representing a second projected image; and means for displaying said second projected image on said display monitor.

10. A method for three-dimensional imaging of ultrasound scattering matter in an object volume, comprising the steps of:

transmitting ultrasound beams into said object volume;

detecting ultrasound echoes reflected from the object volume in response to the transmission of ultrasound beams;

controlling the azimuthal focus of the transmitted ultrasound beams to achieve changes in focal depth;

controlling the elevational focus of the transmitted ultrasound beams as a function of said focal depth;

adjusting a characteristic of a transmit waveform as a function of said focal depth;

coordinating the changes in azimuthal and elevational focus and the adjustments to the transmit waveform characteristic to acquire a source volume of pixel data derived from sample volumes in said object volume;

retrieving a set of pixel data from said source volume, said pixel data set corresponding to a volume of interest in the object volume;

projecting said pixel data set onto a first image plane, thereby forming a projected data set representing a first projected image; and displaying said first projected image.

11. The method as defined in claim 10, wherein said pixel data comprises B-mode intensity data.

12. The method as defined in claim 10, wherein said pixel data comprises velocity data.

13. The method as defined in claim 10, wherein said pixel data comprises power Doppler data.

14. The method as defined in claim 10, wherein the burst length of the transmit waveform is increased with an increase in focal depth.

15. The method as defined in claim 10, wherein the frequency of the transmit waveform is decreased with an increase in focal depth.

16. The method as defined in claim 10, wherein ultrasound beams are transmitted and received by a transducer array operated with a lateral aperture having an f-number less than 1.5.

17. The method as defined in claim 10, wherein ultrasound beams are transmitted and received by a transducer array operated with an elevation aperture which is increased with an increase in focal depth.

18. The method as defined in claim 10, further comprising the steps of:

projecting said pixel data set onto a second image plane which is rotated relative to said first image plane, thereby forming a projected data set representing a second projected image; and displaying said second projected image.

* * * * *